United States Patent [19]

Brown

[11] 3,949,939

[45] Apr. 13, 1976

[54] METERED SPRAY DEVICE

[75] Inventor: Frank E. Brown, Burbank, Calif.

[73] Assignee: SmithKline Corporation, Philadelphia, Pa.

[22] Filed: Mar. 26, 1975

[21] Appl. No.: 562,092

[52] U.S. Cl. .............................. 239/350; 222/424.5
[51] Int. Cl.² ....................... B05B 7/30; G01F 11/28
[58] Field of Search ................. 239/350, 342, 337; 222/424.5

[56] References Cited
UNITED STATES PATENTS

| | | | |
|---|---|---|---|
| 2,892,576 | 6/1959 | Ward | 239/350 |
| 3,341,082 | 9/1967 | Meshberg | 239/350 |
| 3,680,790 | 8/1972 | Boris | 239/350 |
| 3,756,474 | 9/1973 | Riccio | 239/350 |
| 3,797,748 | 3/1974 | Nozawa et al. | 239/350 |
| 3,799,448 | 3/1974 | Nozawa et al. | 239/350 |
| 3,818,908 | 6/1974 | Phillips | 239/350 |

*Primary Examiner*—Lloyd L. King
*Attorney, Agent, or Firm*—Smith, Harding, Earley & Follmer

[57] ABSTRACT

A metered spray device has a container with an open top. A barrel is sealed in the top of the container and extends into the container. An elongated piston is slidably mounted in the barrel. The piston has a central opening running the full length of the piston for the passage of fluid. A check valve in the lower end of the barrel blocks the flow of fluid from the barrel into the container. A nozzle for engagement with a nostril is connected to the upper end of the piston. A spring biased check valve in the upper end of the piston blocks the flow of fluid downwardly into the piston.

8 Claims, 11 Drawing Figures

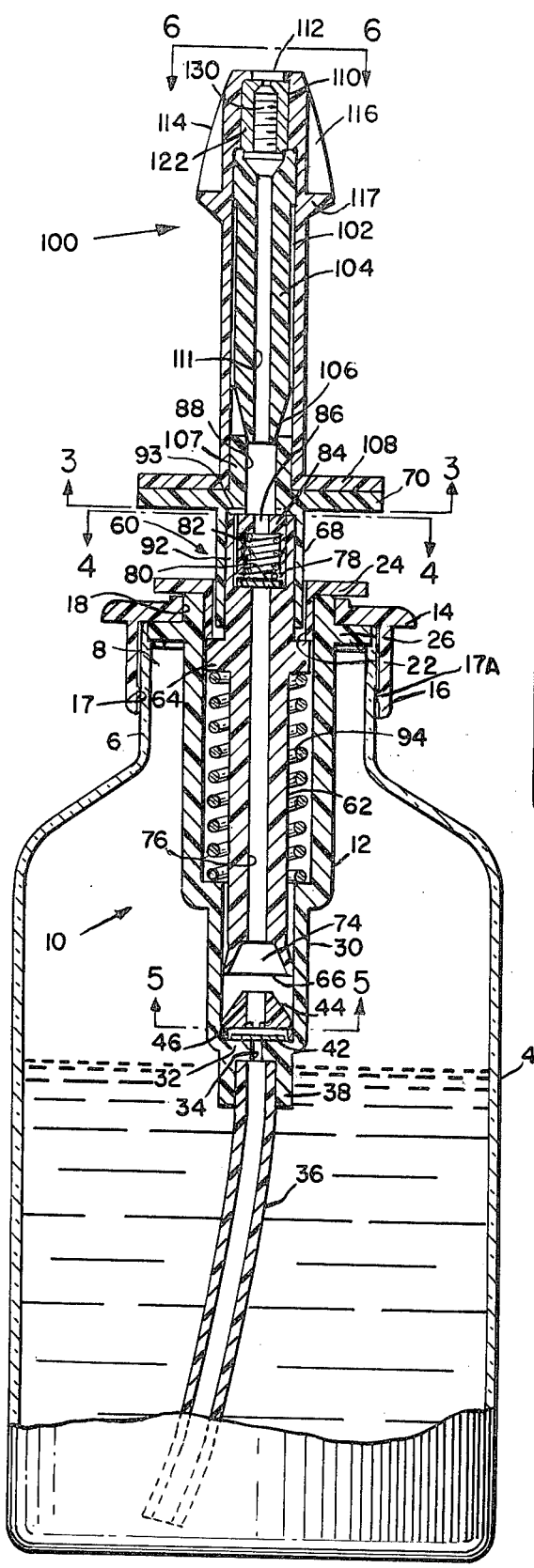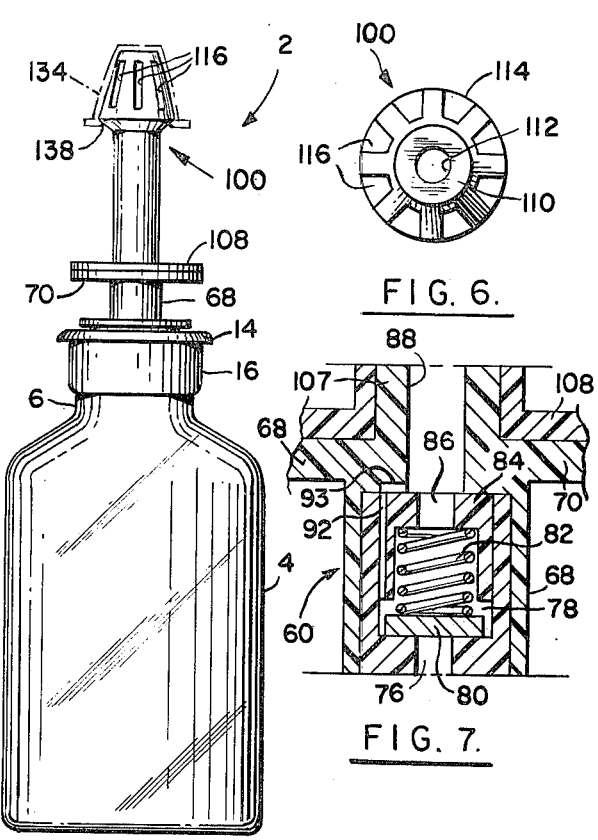
FIG. 1.
FIG. 2.
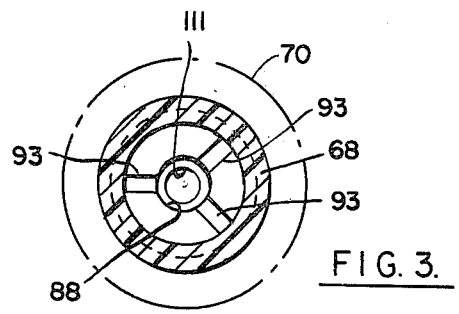
FIG. 6.
FIG. 7.
FIG. 3.
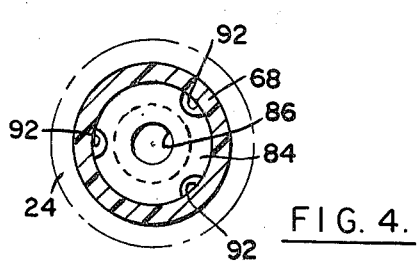
FIG. 4.
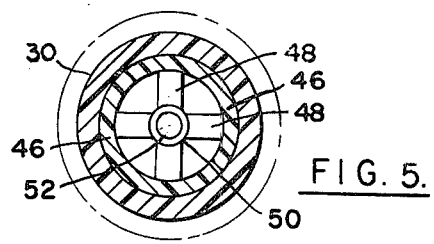
FIG. 5.

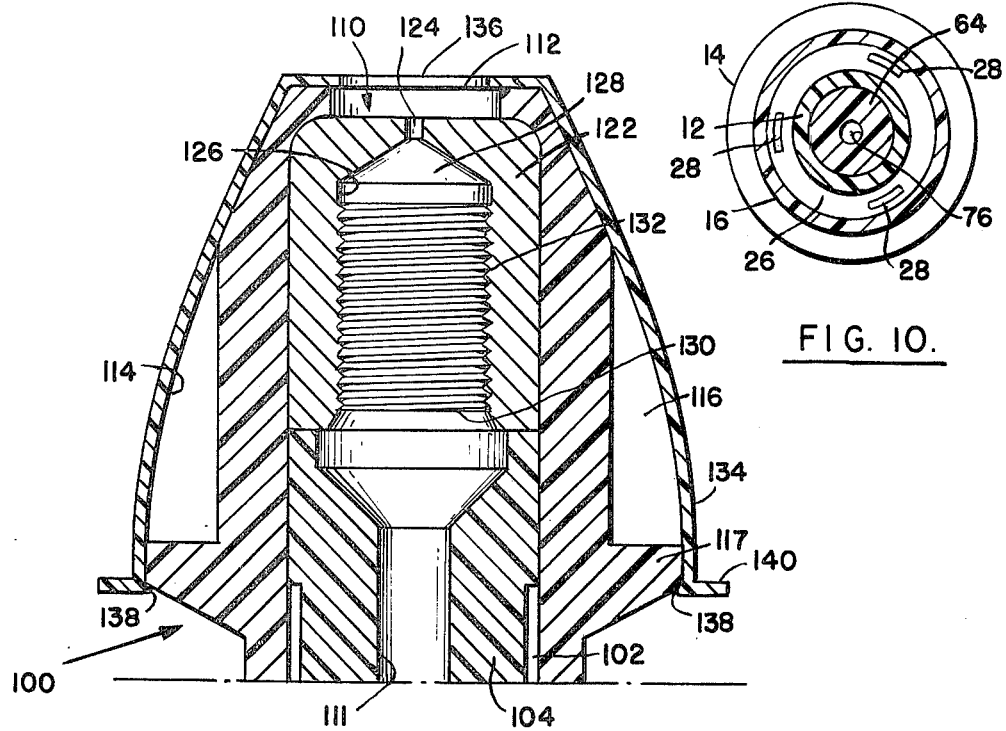
FIG. 8.
FIG. 10.
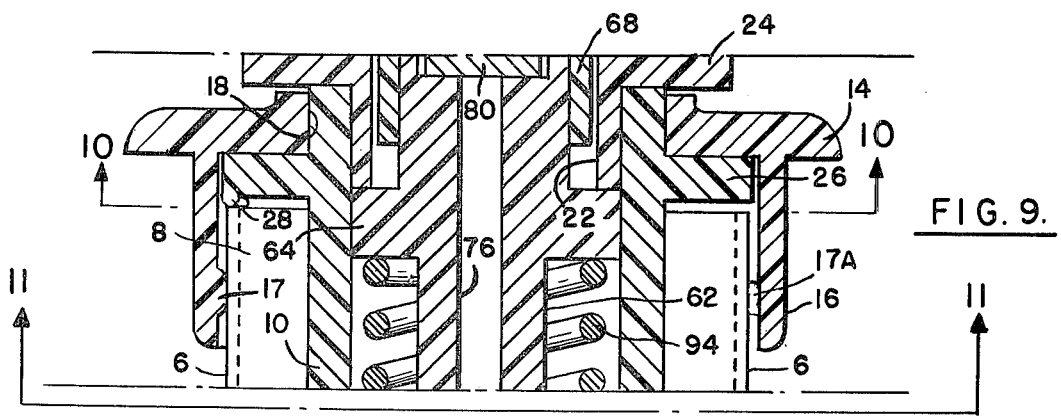
FIG. 9.
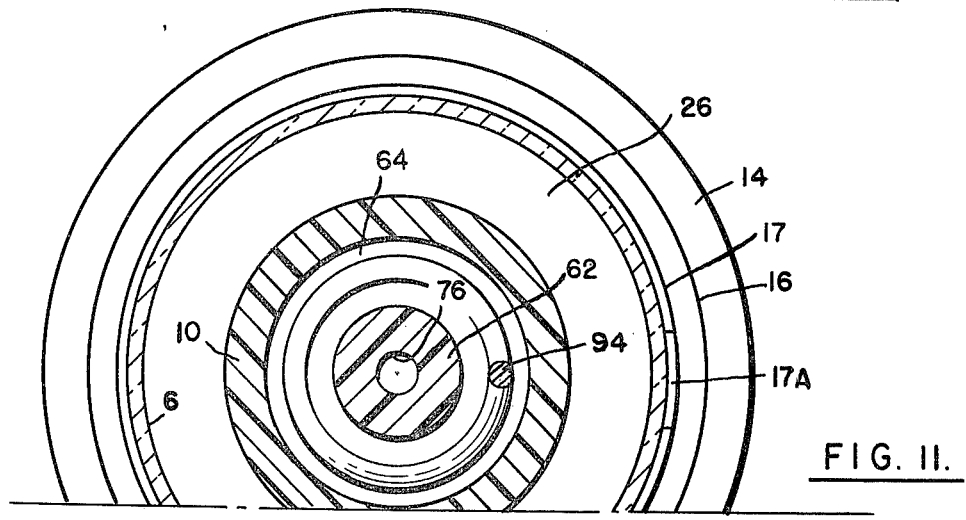
FIG. 11.

3,949,939

METERED SPRAY DEVICE

BACKGROUND OF THE INVENTION

It is known to pump fluid through a spray nozzle into, for example, a patient's nostril.

The device of this invention is advantageous in that it provides a metered amount of liquid to provide a fixed control dosage which cannot be altered by the user. It is also advantageous in that no springs or the like remain in continuous contact with the liquid being dispensed. The check valve arrangement is such that no discharged liquid will be sucked back to contaminate the next amount of liquid to be dispensed and there is a minimum resistance to picking up liquid for the next dispensing operation. Advantageously, a removable cap prevents contamination of one patient by another. The container has venting means and the device has means to deliver a swirling spray.

BRIEF SUMMARY OF THE INVENTION

A metered spray device has a container with an open top. A barrel is sealed in the top of the container and extends into the container. An elongated piston is slidably mounted in the barrel with its lower end engaging the inner wall of the barrel. The piston has a central opening running the full length of the piston for the passage of fluid. A check valve in the lower end of the barrel blocks the flow of fluid from the barrel into the container. A discharge nozzle is connected to the upper end of the piston. The device preferably has additional advantageous features. A spring biased check valve in the upper end of the piston blocks the flow of fluid downwardly into the piston. A spring exterior of the piston biases the piston towards its retracted position. The container has venting means. The device has means to deliver a swirling spray. A removable nozzle cap prevents cross contamination of patients.

BRIEF DESCRIPTION OF THE DRAWINGS

FIG. 1 is an elevational view of a metered nasal spray device in accordance with the invention which has a symmetrical exterior;

FIG. 2 is a vertical section through the device of FIG. 1;

FIG. 3 is a horizontal section taken on the plane indicated by the line 3—3 in FIG. 1;

FIG. 4 is a horizontal section taken on the plane indicated by the line 4—4 in FIG. 1;

FIG. 5 is a horizontal section taken on the plane indicated by the line 5—5 in FIG. 1;

FIG. 6 is a top plan view of the tip of the device of FIG. 1;

FIG. 7 is a vertical section partially broken away showing the upper check valve arrangement of the device of FIG. 1;

FIG. 8 is a enlarged vertical section partially broken away of the nozzle of the device of FIG. 1;

FIG. 9 is a vertical section partially broken away of the device of FIG. 1 in the region of the top of the bottle;

FIG. 10 is a section taken on the plane indicated by the line 10—10 in FIG. 9; and FIG. 11 is a section partially broken away taken on the plane indicated by the line 11—11 in FIG. 9.

DETAILED DESCRIPTION

A metered nasal spray device 2 has a container 4 with a neck 6 and an open upper end 8.

A barrel 10 having an enlarged upper portion 12 is secured to container 4 by a closure member 14 having a wall 16 from which protrudes a bead (FIG. 9) engaging neck 6 by a pressed fit and keeping wall 16 spaced from neck 6. Bead 17 has a cut out portion 17A for the passage of air. Closure member 14 has a central opening 18 in which barrel 10 is mounted and retained by a ring member 22 which has a top flange 24 which engages the upper end of barrel 10. Barrel 10 has a flange 26 which engages the lower face of closure member 14. Flange 26 has three depending bosses 28 which engage the top of bottle neck 6 (FIGS. 9 and 10) and keep it spaced from flange 26.

Barrel 10 has a lower reduced portion 30 and a lower end 32 containing a passage 34 which communicates with the interior of barrel 10 and also with a flexible tube 36 which extends downwardly to a point near the bottom of container 4. Tube 36 is secured to the lower end of barrel 10 by a skirt 38 which extends below lower end 32 of barrel 10. A check valve disc 42 lies on the lower end 32 of barrel 10 and overlies opening 34. A retainer 44 (FIGS. 2 and 5) for check valve 42 has a lower peripheral portion 46 seated on lower barrel portion 32 and is in the form of a spider having four legs 48 connected to the portion 46 and a central portion 50 having a central opening 52 (FIG. 5).

Mounted in barrel 10 and passing through ring member 22 is a piston 60 having a cylindrical portion 62 with a flange 64 adapted to guide piston 60 in cooperation with portion 12 of barrel 10. The lower enlarged end 66 of piston 60 flares outwardly to engage the inner wall of reduced portion 30 of barrel 10 to provide a sliding fluid tight connection. The upper end of piston 60 is formed by a cylindrical member 68 which is telescoped over piston portion 62 and has adjacent its upper end a flange 70.

The lower end 66 of piston 60 has an enlarged opening 74 in the shape of a truncated cone to permit the entry therein of check valve retainer 44. Opening 74 communicates with a smaller bore 76 which extends upwardly through piston 60 to an enlarged opening 78 containing a disc check valve 80 (FIGS. 2 and 7) spring biased downwardly by a compression coil spring 82 which also abuts against a ring insert 84 secured in opening 78 by a pressed fit and having a reduced opening 86 in its upper end which communicates with bore 88 in member 68. As best seen in FIG. 4 ring insert 84 has a plurality of vertically extending openings 92 in its periphery to permit the passage of fluid therethrough into openings 93 in member 68 (FIG. 3). A compression coil spring 94 abutting flange 64 and reduced barrel portion 30 biases piston 60 upwardly as viewed in FIG. 2.

A nozzle 100 has a bore 102 which carries a member 104 secured therein by a pressed fit. Member 104 has a tapered end 106 which enters into bore 88. Nozzle 100 is telescoped over the upper cylindrical portion 107 of member 68 and has a flange 108 coextensive with flange 70 and abutting said flange. A sprayspinner head 110 is mounted in the upper end of nozzle 100 in a position to communicate with bore 111 of member 104 and with the opening 112 in the top 114 of nozzle 100 which is shaped to engage a nostril and has flutes 116 and a flange portion 117.

Spray-spinner head 110 has an outer holding member 122 with an opening 124 (FIG. 8) below opening 112 and communicating with an enlarged bore 126 in member 122. The upper portion 128 of bore 126 is conical. A threaded member 130 (FIG. 8) having threads 132 is seated in bore 126 below the upper portion 128 by a pressed fit. Threads 132 and member 122 form an extended helical passage for the transformation of the fluid into a whirling spray.

A disposable cap 134 (FIG. 8) has an opening 136 above opening 112. Cap 134 has a bead 138 at its lower end which snaps under flange portion 117. A flange 140 opposite bead 138 facilitates removal of cap 134.

The parts shown in the drawings as made of a synthetic resin may be, for example, polyethylene or polypropylene. Materials other than synthetic resins may be employed, for example, metals and glass provided, however, that the cap 134 is advantageously of a resilient material.

OPERATION

Container 4 is filled with the liquid to be dispensed. The remaining parts which have been preassembled are then attached to the container by urging wall 16 of closure member 14 downwardly around the neck 6 of container 4 with bead 17 in contact with neck 6. A pair of fingers are then employed to depress flange 108 against the force of spring 94 and the flange is then released to cause the upward movement of piston 60 by spring 94 to suck up liquid from container 4 through tube 36, opening 34, past check valve 42 and between the legs 48 of check valve retainer 44 into the lower portions of barrel 10 and piston 60. As liquid is sucked out of container 4, air passes between bottle neck 6 and wall 16 being free to pass bead 17 through cut out portion 17A and then passes between the top of neck 16 and flange 26 into container 4. The liquid forces check valve 42 closed after piston 60 stops moving. In order now to dispense the dosage thus accumulated in the lower portions of piston 60 and barrel 10, the container 4 is elevated to place the top 114 of nozzle 100 partially into a nostril and flange 108 is depressed smartly causing the downward movement of piston 60 which maintains check valve 42 in the closed position and causes the liquid in lower portion of barrel 10 and piston 60 to be forced upwardly through bore 76 to open check valve 80 and pass through openings 92 in ring insert 84, openings 93 in member 68, opening 86, bore 88, bore 111, through the helical passage formed by threads 132 and member 122, into the upper portion 128 of bore 126 in a swirling fashion, out through opening 124 and then out through openings 112 and 136 into the interior of the selected nostril. When the dose has been administered spring 82 will close check valve 80 to prevent material from running back downwardly beyond check valve 80 into bore 76 to contaminate a future dose. The release of flange 108 permits spring 94 to move piston 60 upwardly to its original position thus pulling up a new dose from container 4 into barrel 10 and piston 60.

It will be understood that the above embodiment is illustrative and not limiting.

I claim:

1. A metered spray device comprising:
    a container having an open top,
    a barrel sealed in the top of the container and extending into the container,
    an elongated piston slidably mounted in the barrel with its lower end engaging the inner wall of the barrel,
    said piston having a passage running the full length of the piston,
    spring means exterior of the piston to bias the piston towards its retracted position,
    a check valve in the lower end of the barrel to block the flow of fluid from the barrel into the container,
    a discharge nozzle connected to the upper end of the piston, and
    a disc check valve in the upper end of the piston and a spring biasing the disc check valve downwardly to a closed position to block the flow of fluid downwardly in the passage of the piston.

2. The device of claim 1 in which the spring means is within the barrel.

3. The device of claim 1 having venting means connecting the interior of the container to the atmosphere.

4. The device of claim 1 in which the barrel is sealed in the top of the container by a closure member having a top, a depending wall, bosses depending from the top to engage the container and space it away from the closure member, a bead on the inside of the wall to engage the container, said bead having a cut out portion to permit air to pass the bead and flow between the closure member and the container into the container.

5. The device of claim 1 having a removable nozzle cap.

6. The device of claim 1 having means providing a helical passage in the nozzle to form a swirling spray.

7. The device of claim 2 having a flange on the piston above the barrel and above the container for moving the piston towards the bottom of the barrel.

8. The device of claim 6 comprising a threaded member secured by a pressed fit in the bore of a holding member.

* * * * *